United States Patent
Azizian

(10) Patent No.: US 12,102,391 B2
(45) Date of Patent: Oct. 1, 2024

(54) SYSTEM AND METHOD FOR REGISTRATION AND COORDINATED MANIPULATION OF AUGMENTED REALITY IMAGE COMPONENTS

(71) Applicant: INTUITIVE SURGICAL OPERATIONS, INC., Sunnyvale, CA (US)

(72) Inventor: Mahdi Azizian, Santa Clara, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 1026 days.

(21) Appl. No.: 16/465,541

(22) PCT Filed: Jan. 3, 2018

(86) PCT No.: PCT/US2018/012258
§ 371 (c)(1),
(2) Date: May 30, 2019

(87) PCT Pub. No.: WO2018/129094
PCT Pub. Date: Jul. 12, 2018

(65) Prior Publication Data
US 2020/0093544 A1 Mar. 26, 2020

Related U.S. Application Data

(60) Provisional application No. 62/443,460, filed on Jan. 6, 2017, provisional application No. 62/538,425, filed on Jul. 28, 2017.

(51) Int. Cl.
*A61B 34/20* (2016.01)
*A61B 1/00* (2006.01)
(Continued)

(52) U.S. Cl.
CPC ............ *A61B 34/20* (2016.02); *A61B 1/0005* (2013.01); *A61B 1/043* (2013.01); *A61B 34/25* (2016.02);
(Continued)

(58) Field of Classification Search
CPC ....... A61B 34/20; A61B 34/30; A61B 1/0005; A61B 2090/365; G16H 50/50
See application file for complete search history.

(56) References Cited

U.S. PATENT DOCUMENTS

2003/0179308 A1* 9/2003 Zamorano ................ A61B 5/00
                                                         348/333.12
2009/0270678 A1* 10/2009 Scott .................... A61B 90/361
                                                         600/109

(Continued)

FOREIGN PATENT DOCUMENTS

| WO | WO-2013044182 A1 | 3/2013 |
| WO | WO-2015149042 A1 | 10/2015 |
| WO | WO-2016066759 A1 | 5/2016 |

OTHER PUBLICATIONS

"Augmented Reality During Robot-Assisted Laparoscopic Partial Nephrectomy: Toward Real-Time 3D-CT to Stereoscopic Video Registration" by L. Su et al. Urology. 73(4). pp. 896-900. 2008 (Year: 2008).*

(Continued)

*Primary Examiner* — Jason M Ip
(74) *Attorney, Agent, or Firm* — Artegis Law Group, LLP

(57) ABSTRACT

A system and method for registration and coordinated manipulation of augmented reality image components includes registering a model of patient anatomy to a first image of the patient anatomy captured using an imaging device to determine a baseline relationship between the model and the first image, tracking movement of a computer-assisted device used to manipulate the imaging device, (Continued)

updating the baseline relationship based on the tracked movement, and generating a composite image by overlaying the model on a second image of the patient anatomy according to the updated relationship. In some embodiments, the model is semi-transparent. In some embodiments, registering the model to the first image includes adjusting the model relative to the first image based on one or more inputs received from a user and generating a model to image transformation based on the adjustments to the model. The model to image transformation captures the baseline relationship.

22 Claims, 5 Drawing Sheets

(51) Int. Cl.
```
A61B 1/04       (2006.01)
A61B 34/00      (2016.01)
A61B 34/30      (2016.01)
A61B 90/00      (2016.01)
G06F 3/04883    (2022.01)
G06T 7/00       (2017.01)
G06T 11/60      (2006.01)
G16H 30/40      (2018.01)
G16H 50/50      (2018.01)
```
(52) U.S. Cl.
CPC .............. *A61B 34/30* (2016.02); *A61B 90/36* (2016.02); *G06F 3/04883* (2013.01); *G06T 7/0012* (2013.01); *G06T 11/60* (2013.01); *G16H 30/40* (2018.01); *G16H 50/50* (2018.01); *A61B 2034/2065* (2016.02); *A61B 2034/301* (2016.02); *A61B 2090/365* (2016.02); *G06T 2207/10064* (2013.01); *G06T 2207/10068* (2013.01); *G06T 2207/10081* (2013.01); *G06T 2207/30008* (2013.01); *G06T 2207/30096* (2013.01); *G06T 2211/428* (2013.01)

(56) References Cited

U.S. PATENT DOCUMENTS

| | | | | |
|---|---|---|---|---|
| 2012/0134562 | A1* | 5/2012 | Boettger | G06T 17/00 |
| | | | | 382/131 |
| 2012/0289777 | A1* | 11/2012 | Chopra | A61B 5/6852 |
| | | | | 382/128 |
| 2013/0006421 | A1* | 1/2013 | Brogardh | B25J 9/1692 |
| | | | | 700/254 |
| 2013/0063434 | A1 | 3/2013 | Miga et al. | |
| 2014/0072170 | A1* | 3/2014 | Zhang | G06V 20/53 |
| | | | | 382/103 |
| 2014/0276002 | A1 | 9/2014 | West et al. | |
| 2015/0055085 | A1 | 2/2015 | Fonte et al. | |
| 2016/0191887 | A1* | 6/2016 | Casas | H04N 13/111 |
| | | | | 348/47 |

OTHER PUBLICATIONS

International Search Report and Written Opinion for Application No. PCT/US2018/012258, mailed on Apr. 18, 2018, 14 pages.
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.
Extended European Search Report for Application No. EP18736619.0 mailed on Jul. 21, 2020, 12 pages.

* cited by examiner

SYSTEM AND METHOD FOR REGISTRATION AND COORDINATED MANIPULATION OF AUGMENTED REALITY IMAGE COMPONENTS

RELATED APPLICATIONS

This patent application claims priority to and benefit of the filing date of U.S. Provisional Patent Application No. 62/443,460, entitled "Registration and Coordinated Manipulation of Augmented Reality Image Components," filed Jan. 6, 2017, and to U.S. Provisional Patent Application No. 62/538,425, entitled "System and Method for Registration and Coordinated Manipulation of Augmented Reality Image Components," filed Jul. 28, 2017, which are hereby incorporated by reference in their entirety.

TECHNICAL FIELD

Inventive aspects are directed towards augmented reality technologies. In one embodiment, an imaging system is provided for use during the performance of minimally-invasive surgical procedures.

BACKGROUND

The rise of minimally invasive surgery beginning in the 20th century has afforded patients with certain ailments a less traumatic surgical treatment option. One type of minimally invasive surgery, laparoscopy, involves the use of an endoscope (type of imaging device) to image the internals of a patient. Treatment is provided using surgical instruments provided at the end of long, thin shafts. Minimally-invasive surgery was revolutionized with the advent of computer-assisted surgical systems, such as the da Vinci Surgical System commercialized by Intuitive Surgical. One innovation of the da Vinci Surgical System is the inclusion of a stereoscopic endoscope. When a user views the resulting stereoscopic image of patient anatomy, the user perceives a 3D scene. The view, however, is limited to the surfaces of the patient anatomy visible to the endoscope and typically does not give the surgeon or other medical personnel a complete view of the relevant patient anatomy as subsurface features are hidden. Information on the sub-surface features is available through separately obtained images obtained either pre-operatively or inter-operatively using other imaging modalities, such as computed tomography (CT), magnetic resonance imaging (MRI), fluoroscopy, thermography, ultrasound, optical coherence tomography (OCT), thermal imaging, impedance imaging, laser imaging, nanotube X-ray imaging, and/or the like. Unfortunately, it not always easy to determine an alignment or registration between the endoscope images and these separately obtained images.

Accordingly, it would be advantageous to have systems and methods for combining the endoscope and other images into a composite view that could simultaneously show both the surface and sub-surface features of the patient anatomy. One such approach is to use augmented reality imaging technologies that create composite images by combining endoscope images with patient-specific models of the patient anatomy determined using the other imaging modalities. This provides the surgeon or other medical personnel the capability to visualize the anatomical structure of tissue that lies beneath the tissue surface captured in the endoscope image.

SUMMARY

The following summary introduces certain aspects of the inventive subject matter in order to provide a basic understanding. This summary is not an extensive overview of the inventive subject matter, and it is not intended to identify key or critical elements or to delineate the scope of the inventive subject matter. Although this summary contains information that is relevant to various aspects and embodiments of the inventive subject matter, its sole purpose is to present some aspects and embodiments in a general form as a prelude to the more detailed description below.

In one embodiment, an augmented reality imaging system is integrated with a computer-assisted surgical system, a da Vinci Surgical System. The da Vinci Surgical System can include one or more robotic manipulators. An endoscope or a therapeutic surgical instrument can be mounted on each of the one or more robotic manipulator. The one or more robotic manipulators are used to position or orient an endoscope or a therapeutic surgical instrument mounted thereon. The robotic manipulators move in response to movements by a user of one or more master manipulators. In this way, the user can control the position or orientation of the endoscope or therapeutic surgical instrument mounted on any given robotic manipulator.

In one embodiment, an augmented reality imaging system is integrated with a computer-assisted surgical system. A preoperative or intraoperative tomographic scan is taken of a given patient. A computer model is generated from this tomographic scan. This patient then undergoes a surgical procedure using a computer-assisted surgical system, such as a da Vinci Surgical System. During this surgical procedure, an endoscope is used to provide the surgeon performing the operation with real time images of a surgical site. These real time images can be augmented with a computer model of patient anatomy generated from the tomographic scan. For example, a composite image can be created in which the computer model is overlaid on top of the endoscope image. The computer model can provide the surgeon with additional information beyond what can be visibly seen from the endoscope image. For example, the computer model can provide information of certain subsurface anatomical structures (e.g., vessels, ducts, calyces, bones, tumors, etc.).

A useful composite image includes the computer model component of the composite image and the endoscope image component of the composite image being correctly registered, or aligned. During a typical surgical procedure, the endoscope captures, within its field of view, images of certain patient anatomy. When the endoscope position is moved, the patient anatomy captured within the endoscopes field of view changes. For the composite image to remain accurate, the computer model component of the composite image component is adjusted accordingly to account for the endoscope movement. Several inventive aspects disclosed in the instant patent application provide an approach for accomplishing this challenge.

In one aspect, a computer-assisted surgical system including an endoscope is provided. At the start of a surgical procedure, the endoscope is at an initial position and captures within its field of view an initial endoscope image of a surgical site. A user of the surgical system is presented with a computer model of the anatomy, the computer model including the surgical site and nearby anatomy. The computer model of the anatomy can be overlaid on top of the endoscope image to create the composite image. A user input device, e.g., a tablet touchscreen interface, is provided to allow the user to manipulate (e.g., zoom in/out, rotate, etc.) the computer model component of the composite image, leaving undisturbed the endoscope image component of the composite image. When the user is satisfied with the alignment of the computer model component and the endoscope image component, the user locks the alignment of the two components.

Once initial alignment of the computer model component and the endoscope image component is completed, the scaling of the computer model component of the composite image has been adjusted to correspond to that of the endoscope image and the coordinate system of the computer model has been aligned with the coordinate system of the endoscope image. In one instance, viewing a composite image is desired. A user commands a movement of the endoscope, causing a change in the endoscope image component of the composite image. The commanded movement involves the synchronized movement of various joints of the robotic manipulator on which the endoscope is mounted. The amount that each joint is moved is a form of kinematic data that describes the change in position of the endoscope, and accordingly, the change to the endoscope image captured by the endoscope. In the case in which initial alignment of the computer model component and the endoscope image component of the composite image has already been completed, kinematic data associated with a change to the endoscope image component of a composite image can be used to produce a matching, coordinated movement of the computer model component of the composite image. This method, termed kinematic tracking, preserves the alignment between the computer model component and the endoscope image component when the endoscope is moved during a surgical procedure. A chain of transformations used to perform this kinematic tracking are detailed below.

Consistent with some embodiments, a method of generating augmented reality images includes registering a model of patient anatomy to a first image of the patient anatomy captured using an imaging device to determine a baseline relationship between the model and the first image, tracking movement of a computer-assisted device used to manipulate the imaging device, updating the baseline relationship based on the tracked movement, and generating a composite image by overlaying the model on a second image of the patient anatomy according to the updated relationship.

Consistent with some embodiments, a computer-assisted medical device includes an articulated arm, an imaging device mounted on the articulated arm, and a processor coupled to the articulated arm and the imaging device. The processor is configured to register a model of patient anatomy to a first image of the patient anatomy captured using the imaging device to determine a baseline relationship between the model and image, track movement of the imaging device, update the baseline relationship based on the tracked movement, and generate a composite image by overlaying the model on a second image of the patient anatomy according to the updated relationship.

Consistent with some embodiments, a non-transitory computer-readable medium having stored thereon a plurality of machine-readable instructions which when executed by one or more processors associated with a computer-assisted device are adapted to cause the one or more processors to perform a method. The method includes registering a model of patient anatomy to a first image of the patient anatomy captured using an imaging device to determine a baseline relationship between the model and the first image, tracking movement of a computer-assisted device used to manipulate the imaging device, updating the baseline relationship based on the tracked movement, and generating a composite image by overlaying the model on a second image of the patient anatomy according to the updated relationship.

Figure 1:
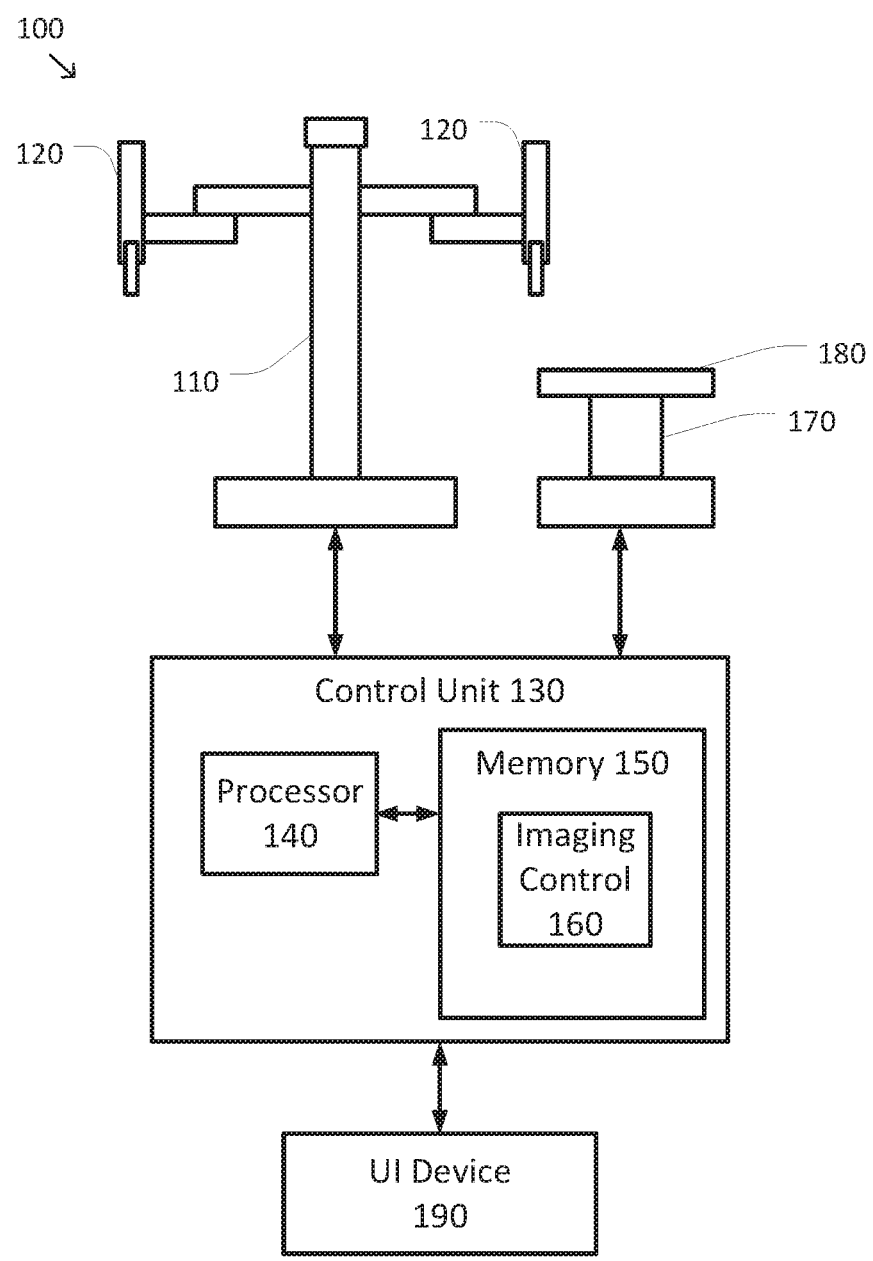
FIG. 1 is a simplified diagram of a computer-assisted system according to some embodiments.

Embodiments of the present disclosure and their advantages are best understood by referring to the detailed description that follows. It should be appreciated that like reference numerals are used to identify like elements illustrated in one or more of the figures, wherein showings therein are for purposes of illustrating embodiments of the present disclosure and not for purposes of limiting the same.

DETAILED DESCRIPTION

This description and the accompanying drawings that illustrate inventive aspects, embodiments, implementations, or applications should not be taken as limiting—the claims define the protected invention. Various mechanical, compositional, structural, electrical, and operational changes may be made without departing from the spirit and scope of this description and the claims. In some instances, well-known circuits, structures, or techniques have not been shown or described in detail in order not to obscure the invention. Like numbers in two or more figures represent the same or similar elements.

In this description, specific details are set forth describing some embodiments consistent with the present disclosure. Numerous specific details are set forth in order to provide a thorough understanding of the embodiments. It will be apparent, however, to one skilled in the art that some embodiments may be practiced without some or all of these specific details. The specific embodiments disclosed herein are meant to be illustrative but not limiting. One skilled in the art may realize other elements that, although not specifically described here, are within the scope and the spirit of this disclosure. In addition, to avoid unnecessary repetition, one or more features shown and described in association with one embodiment may be incorporated into other embodiments unless specifically described otherwise or if the one or more features would make an embodiment non-functional.

Further, this description's terminology is not intended to limit the invention. For example, spatially relative terms-such as "beneath", "below", "lower", "above", "upper", "proximal", "distal", and the like—may be used to describe one element's or feature's relationship to another element or feature as illustrated in the figures. These spatially relative terms are intended to encompass different positions (i.e., locations and orientations (i.e., rotational placements) of a device in use or operation in addition to the position and orientation shown in the figures. For example, if a device in the figures is turned over, elements described as "below" or "beneath" other elements or features would then be "above" or "over" the other elements or features. Thus, the exemplary term "below" can encompass both positions and orientations of above and below. A device may be otherwise oriented (rotated 90 degrees or at other orientations) and the spatially relative descriptors used herein interpreted accordingly. Likewise, descriptions of movement along and around various axes include various special device positions and orientations. In addition, the singular forms "a", "an", and "the" are intended to include the plural forms as well, unless the context indicates otherwise. And, the terms "comprises", "comprising", "includes", and the like specify the presence of stated features, steps, operations, elements, and/or components but do not preclude the presence or addition of one or more other features, steps, operations, elements, components, and/or groups. Components described as coupled may be electrically or mechanically directly coupled, or they may be indirectly coupled via one or more intermediate components.

Elements described in detail with reference to one embodiment, implementation, or application may, whenever practical, be included in other embodiments, implementations, or applications in which they are not specifically shown or described. For example, if an element is described in detail with reference to one embodiment and is not described with reference to a second embodiment, the element may nevertheless be claimed as included in the second embodiment. Thus, to avoid unnecessary repetition in the following description, one or more elements shown and described in association with one embodiment, implementation, or application may be incorporated into other embodiments, implementations, or aspects unless specifically described otherwise, unless the one or more elements would make an embodiment or implementation non-functional, or unless two or more of the elements provide conflicting functions.

The term "flexible" in association with a part, such as a mechanical structure, component, or component assembly, should be broadly construed. In essence, the term means the part can be repeatedly bent and restored to an original shape without harm to the part. Many "rigid" objects have a slight inherent resilient "bendiness" due to material properties, although such objects are not considered "flexible" as the term is used herein. A flexible part may have infinite degrees of freedom (DOE's). Examples of such parts include closed, bendable tubes (made from, e.g., NITINOL, polymer, soft rubber, and the like), helical coil springs, etc. that can be bent into various simple or compound curves, often without significant cross-sectional deformation. Other flexible parts may approximate such an infinite-DOF part by using a series of closely spaced components that are similar to a snake-like arrangement of serial "vertebrae". In such a vertebral arrangement, each component is a short link in a kinematic chain, and movable mechanical constraints (e.g., pin hinge, cup and ball, live hinge, and the like) between each link may allow one (e.g., pitch) or two (e.g., pitch and yaw) DOF's of relative movement between the links. A short, flexible part may serve as, and be modeled as, a single mechanical constraint (joint) that provides one or more DOF's between two links in a kinematic chain, even though the flexible part itself may be a kinematic chain made of several coupled links. Knowledgeable persons will understand that a part's flexibility may be expressed in terms of its stiffness.

Unless otherwise stated in this description, a flexible part, such as a mechanical structure, component, or component assembly, may be either actively or passively flexible. An actively flexible part may be bent by using forces inherently associated with the part itself. For example, one or more tendons may be routed lengthwise along the part and offset from the part's longitudinal axis, so that tension on the one or more tendons causes the part or a portion of the part to bend. Other ways of actively bending an actively flexible part include, without limitation, the use of pneumatic or hydraulic power, gears, electroactive polymer (more generally, "artificial muscle"), and the like. A passively flexible part is bent by using a force external to the part (e.g., an applied mechanical or electromagnetic force). A passively flexible part may remain in its bent shape until bent again, or it may have an inherent characteristic that tends to restore the part to an original shape. An example of a passively flexible part with inherent stiffness is a plastic rod or a resilient rubber tube. An actively flexible part, when not actuated by its inherently associated forces, may be passively flexible. A single part may be made of one or more actively and passively flexible parts in series.

In some instances well known methods, procedures, components, and circuits have not been described in detail so as not to unnecessarily obscure aspects of the embodiments.

This disclosure describes various instruments and portions of instruments in terms of their state in three-dimensional space. As used herein, the term "position" refers to the location of an object or a portion of an object in a three-dimensional space (e.g., three degrees of translational freedom along Cartesian x-, y-, and z-coordinates). As used herein, the term "orientation" refers to the rotational placement of an object or a portion of an object (three degrees of rotational freedom—e.g., roll, pitch, and yaw). As used herein, the term "pose" refers to the position of an object or a portion of an object in at least one degree of translational freedom and to the orientation of that object or portion of the object in at least one degree of rotational freedom (up to six total degrees of freedom). As used herein, the term "shape" refers to a set of poses, positions, or orientations measured along an object.

Aspects of the invention are described primarily in terms of an implementation using a da Vinci® Surgical System (specifically, a Model IS4000, marketed as the da Vinci® Xi™ Surgical System), commercialized by Intuitive Surgical, Inc. of Sunnyvale, California, Knowledgeable persons will understand, however, that inventive aspects disclosed herein may be embodied and implemented in various ways, including robotic and, if applicable, non-robotic embodiments and implementations. Implementations on da Vinci® Surgical Systems e.g., the Model IS41000; the Model IS4200, commercialized as the da Vinci® X™ Surgical System) are merely exemplary and are not to be considered as limiting the scope of the inventive aspects disclosed herein. For example, any reference to surgical instruments and surgical methods is non-limiting as the instruments and methods described herein may be used for animals, human cadavers, animal cadavers, portions of human or animal anatomy, non-surgical diagnosis, industrial systems, and general robotic or teleoperational systems.

FIG. 1 is a simplified diagram of a computer-assisted system 100 according to some embodiments. As shown in FIG. 1, computer-assisted system 100 includes a computer-assisted device 110 with one or more movable or articulated arms 120. Each of the one or more articulated arms 120 may support one or more end effectors. In some examples, computer-assisted device 110 may be consistent with a computer-assisted surgical device. The one or more articulated arms 120 may each provide support for one or more tools, surgical instruments, imaging devices, and/or the like mounted to a distal end of at least one of the articulated arms 120. Computer-assisted device 110 may further be coupled to an operator workstation (not shown), which may include one or more master controls for operating computer-assisted device 110, the one or more articulated arms 120, and/or the end effectors. In some embodiments, computer-assisted device 110 and the operator workstation may correspond to a da Vinci® Surgical System commercialized by Intuitive Surgical, Inc. of Sunnyvale, California. In some embodiments, computer-assisted surgical devices with other configurations, fewer or more articulated arms, and/or the like may be used with computer-assisted system 100.

Computer-assisted device 110 is coupled to a control unit 130 via an interface. The interface may include one or more wireless links, cables, connectors, and/or buses and may further include one or more networks with one or more network switching and/or routing devices. Control unit 130 includes a processor 140 coupled to memory 150. Operation of control unit 130 is controlled by processor 140. And although control unit 130 is shown with only one processor 140, it is understood that processor 140 may be representative of one or more central processing units, multi-core processors, microprocessors, microcontrollers, digital signal processors, field programmable gate arrays (FPGAs), application specific integrated circuits (ASICs), and/or the like in control unit 130. Control unit 130 may be implemented as a stand-alone subsystem and/or board added to a computing device or as a virtual machine. In some embodiments, control unit may be included as part of the operator workstation and/or operated separately from, but in coordination with the operator workstation.

Memory 150 may be used to store software executed by control unit 130 and/or one or more data structures used during operation of control unit 130. Memory 150 may include one or more types of machine readable media. Some common forms of machine readable media may include floppy disk, flexible disk, hard disk, magnetic tape, any other magnetic medium, CD-ROM, any other optical medium, RAM, PROM, EPROM, FLASH-EPROM, any other memory chip or cartridge, and/or any other medium from which a processor or computer is adapted to read.

As shown, memory 150 includes an imaging application 160 that may be used to support the imaging techniques described further below that aid an operator, such as a surgeon or other medical personnel in the operation of computer-assisted device 110. Imaging application 160 may include one or more application programming interfaces (APIs) for receiving position, motion, and/or other sensor information from computer-assisted device 110 and/or a surgical table, receiving images and/or models from external sources (not shown), interacting with user interface devices, generating images for display, and/or the like. And although imaging application 160 is depicted as a software application, imaging application 160 may be implemented using hardware, software, and/or a combination of hardware and software.

In some embodiments, computer-assisted system 100 may be found in an operating room and/or an interventional suite. And although computer-assisted system 100 includes only one computer-assisted device 110 with two articulated arms 120, one of ordinary skill would understand that computer-assisted system 100 may include any number of devices with articulated arms and/or end effectors of similar and/or different design from computer-assisted device 110. In some examples, each of the devices may include fewer or more articulated arms and/or end effectors. In some examples, computer-assisted device 110 may be consistent with a da Vinci Surgical System.

Computer-assisted system 100 further includes a surgical table 170. Like the one or more articulated arms 120, surgical table 170 may support articulated movement of a table top 180 relative to a base of surgical table 170. In some examples, the articulated movement of table top 180 may include support for changing a height, a tilt, a slide, a Trendelenburg orientation, and/or the like of table top 180. Although not shown, surgical table 170 may include one or more control inputs, such as a control pendant for controlling the position and/or orientation of table top 180. In some embodiments, surgical table 170 may correspond to one or more of the operating tables commercialized by Trumpf Medical Systems GmbH of Germany.

Surgical table 170 may also be coupled to control unit 130 via a corresponding interface. The interface may include one or more wireless links, cables, connectors, and/or buses and may further include one or more networks with one or more network switching and/or routing devices. In some embodiments, surgical table 170 may be coupled to a different control unit than control unit 130. In some examples, imaging application 160 may include one or more application programming interfaces (APIs) for receiving position, motion, and/or other sensor information associated with surgical table 170 and/or table top 180. In some examples, imaging application 160 may help register computer-assisted device 110 with surgical table 170 so that a geometric relationship between computer-assisted device 110 and surgical table 170 is known. In some examples, the geometric relationship may include a translation and/or one or more rotations between coordinate systems maintained for computer-assisted device 110 and surgical table 170.

Computer-assisted system 100 further includes a user interface (UI) device 190. UI device 190 may also be coupled to control unit 130 via a corresponding interface. The interface may include one or more wireless links, cables, connectors, and/or buses and may further include one or more networks with one or more network switching and/or routing devices. UI device 190 further includes one or more controls and/or other input mechanisms for receiving input and commands from an operator. In some examples, UI device 190 may include a touch-sensitive input mechanism, such as a touch screen, a tablet, a digitizer, a telestrator, and/or the like for receiving the inputs and commands from the operator. UI device 190 further includes one or more display units or screens for displaying various images to the operator as is described in further detail below. In some examples, UI device 190 may include left and right output displays to provide 3D stereoscopic images to an operator. In some examples, the touch-sensitive input mechanism may be combined with or separate from the one or more display screens.

Figure 2:
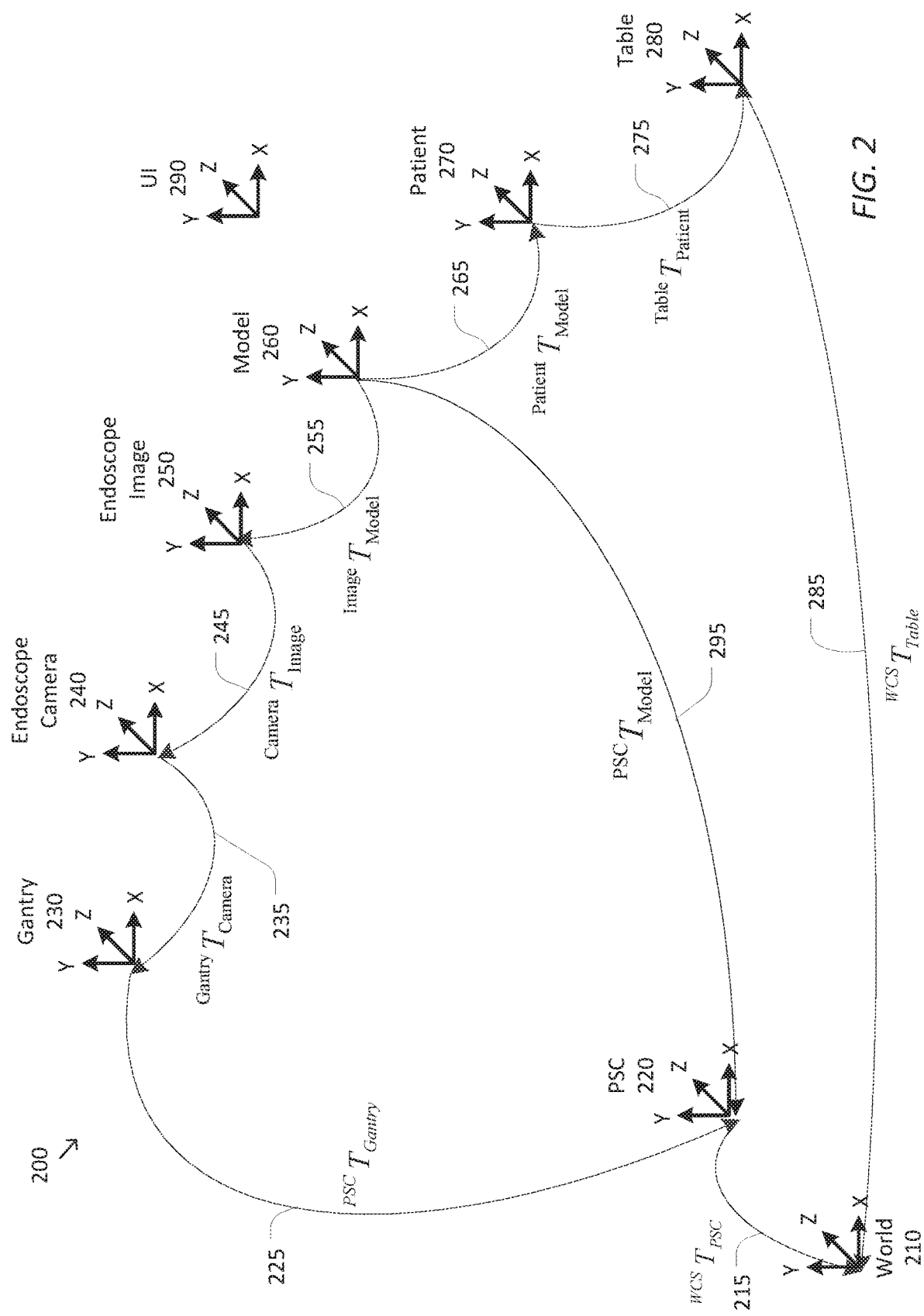
FIG. 2 is a simplified diagram of a kinematic model of a computer-assisted medical system according to some embodiments.

FIG. 2 is a simplified diagram of a kinematic model 200 of a computer-assisted medical system according to some embodiments. As shown in FIG. 2, kinematic model 200 includes kinematic information associated with many sources and/or devices. The kinematic information may be based on known kinematic models for the links and joints of a computer-assisted medical device and a surgical table, such as computer-assisted device 110 and surgical table 170, respectively. The kinematic information may be further based on information associated with the position and/or orientation of the joints of the computer-assisted medical device and the surgical table. In some examples, the information associated with the position and/or orientation of the joints may be derived from one or more sensors, such as encoders and resolvers, measuring the linear positions of prismatic joints and the rotational positions of revolute joints. In some examples, the information associated with relative position and/or orientation of the joints may be derived from external trackers, such as optical trackers, electromagnetic trackers, shape sensors, and/or the like. In some examples, the kinematic information is not known directly and is inferred and/or computed based on the known kinematic information.

Kinematic model 200 includes several coordinate frames or coordinate systems and transformations, such as homogeneous transformations, for transforming positions and/or orientations from one of the coordinate systems to another of the coordinate systems. In some examples, kinematic model 200 is used to permit the forward and/or reverse mapping of positions and/or orientations in one of the coordinate systems in any other of the coordinate systems by composing the forward and/or reverse/inverse transformations noted by the transform linkages included in FIG. 2. In some examples, when the transformations are modeled as homogenous transformations in matrix form, the composing may be accomplished using matrix multiplication. In some embodiments, kinematic model 200 may be used to model the kinematic relationships of computer-assisted device 110 and surgical table 170 of FIG. 1.

As shown in FIG. 2, kinematic model 200 includes a world coordinate system (WCS) 210 acting as a reference coordinate system associated with the operating room, a patient side cart (PSC) coordinate system 220 corresponding to a base coordinate system for a computer-assisted device (such as computer-assisted device 110), a gantry coordinate system 230 corresponding to portion of the computer-assisted device to which one or more manipulators may be mounted, an endoscope camera coordinate system 240 corresponding to a position and orientation of an endoscope, an endoscope image coordinate system 250 corresponding to images obtained using the endoscope, a model coordinate system 260 corresponding to an anatomical model of patient anatomy, a patient coordinate system 270 corresponding to the position and orientation of the patient, and a table coordinate system 280 corresponding to the position and orientation of the surgical table (such as table 170). In some examples, the anatomical model is derived from pre-operative or other images of the patient anatomy. Kinematic model 200 further includes a user interface device system 290 corresponding to a coordinate system used to interpret inputs from the operator used to manipulate the model to help position and orient model coordinate system 260.

Kinematic model 200 further includes several transformations used to model the relationships between the various coordinate systems. Each of the transformations are then used to model various forward and reverse kinematic chains that are usable to support the imaging operations as described further below. Each of the transformations shown in FIG. 2 denotes a "link" in one of the kinematic chains in kinematic model 200 as shown by a corresponding arrow in the figure. Each of the transformations is identified by the coordinate systems it provides a link between, where the A coordinate system to B coordinate transformation (or A-to-B transformation) is represented by $^{B}T_{A}$.

Kinematic model 200 further includes two closed kinematic chains where there is more than one set of transformations that may be used to move between the same two coordinate systems. One closed kinematic chain is between PSC coordinate system 220 and model coordinate system 260. This closed kinematic chain means that the coordinate transformations from model coordinate system 260 through endoscope image coordinate system 250, endoscope camera coordinate system 240, and gantry coordinate system 230 to PSC coordinate system 220 are equivalent to the direct transformation between model coordinate system 260 and PSC coordinate system 220 using model-to-PSC transformation 295. This equivalence is shown in Equation 1. This means that model-to-PSC transformation 295 may be determined from model-to-image transformation 255, image-to-camera transformation 245, camera-to-gantry transformation 235, and gantry-to-PSC transformation 225.

$$^{PSC}T_{Model} = {}^{PSC}T_{Gantry} \cdot {}^{Gantry}T_{Camera} \cdot {}^{Camera}T_{image} \cdot {}^{Image}T_{Model} \quad \text{Equation 1}$$

Another closed kinematic chain includes the loop between world coordinate system 210 and model coordinate system 260. The equivalence of this closed kinematic chain is shown in Equation 2.

$$^{WCS}T_{PSC} \cdot {}^{PSC}T_{Model} = {}^{WCS}T_{Table} \cdot {}^{Table}T_{Patient} \cdot {}^{Patient}T_{Model} \quad \text{Equation 2}$$

According to some embodiments, some observations regarding the transformations are possible. Table-to-WCS transformation 285 is typically not known as the surgical table may typically be moved about and oriented flexibly within the operating room. PSC-to-WCS transformation 215 is typically not known as the computer-assisted device may similarly be moved about and oriented flexibly within the operating room. Patient-to-table transformation 275 is typically not known as the position and the orientation of the patient relative to the surgical table may vary by patient, procedure, surgeon, and/or the like. However, under the assumption that model-to-patient transformation 265 is an identity transformation (i.e., model coordinate system 260 matches patient coordinate system 270) it is possible to use a registration procedure between the computer-assisted device and the surgical table to determine a table-to-PSC transformation (not shown) that creates a closed kinematic chain that allows for world coordinate system 210 to be bypassed and patient-to-table transformation 275 to be computed based on this closed kinematic chain. Several procedures are available for registering the surgical table to the computer-assisted device. Examples of these procedures are described in further detail in commonly owned U.S. patent application Ser. No. 15/522,180, filed on Apr. 26, 2017 and entitled "System and Method for Registering to a Surgical Table," which is hereby incorporated by reference in its entirety.

Gantry-to-PSC transformation 225 and camera-to-gantry transformation 235 are determined from the kinematics and joint sensor signals that are known for the computer-assisted device. Image-to-camera transformation 245 is determined through one or more calibration procedures associated with the endoscope that takes into account the focal length of the endoscope. When the focal length of the endoscope is variable, the one or more calibration procedures may be used to provide corresponding image-to-camera transformations 245 that account for the changes in focal length.

Kinematic model 200 is used in two different phases to support the imaging techniques as described in further detail below. In a first phase, a registration process is used to determine an initial or registered version of model-to-image transformation 255. The registration process includes overlaying the model of the patient anatomy over live endoscope images taken of the same patient anatomy. The operator then manipulates the model using one or more input mechanisms, such as the input mechanisms of UI device 190. When the operator is satisfied that the model is correctly positioned and aligned with the actual anatomy as shown in the overlay, a baseline value for model-to-PSC transformation 295 is determined by capturing the kinematics of the computer-assisted device to determine gantry-to-PSC transformation 225 and camera-to-gantry transformation 235, using the camera calibration information for the endoscope to determine image-to-camera transformation 245, and applying Equation 1. This effectively registers model coordinate system 260 and patient coordinate system 270 so that model-to-patient transformation 265 is an identity transformation. In some examples, little or no movement of the computer-assisted device is typically allowed during the registration process as it can complicate or prolong the registration process, however, the registration may be completed even when gantry-to-PSC transformation 225, camera-to-gantry transformation 235, and image-to-camera transformation 245 are not static as long as at the instant of registration, Equation 1 can be applied to determine the baseline model-to-PSC transformation 295.

In the second phase, the baseline model-to-PSC transformation 295 is used to adjust model-to-image transformation 255 as the operator drives the computer-assisted device and/or adjusts the endoscope (i.e., as gantry-to-PSC transformation 225, camera-to-gantry transformation 235, and image-to-camera transformation 245 change). This is often referred to as tracking. Under the assumption that the surgical table is not moving and the patient is not moving relative to the surgical table, the model-to-PSC transformation 295 is static and does not change. Thus, Equation 1 can be rearranged to describe new updated values for model-to-image transformation 255 that are used to keep the model matched to the endoscope images. This is shown in Equation 3.

$$^{Image}T_{Model} = [^{PSC}T_{Gantry} \cdot {}^{Gantry}T_{Camera} \cdot {}^{Camera}T_{Image}]^{-1} \cdot {}^{PSC}T_{Model} \quad \text{Equation 3}$$

When the surgical table moves or the patient moves relative to the surgical table, model-to-PSC transformation 295 changes and has to be updated. In some examples, model-to-PSC transformation 295 may be updated by repeating the registration process of the first phase. In some examples, the registration between the surgical table and the computer-assisted device and the table-to-PSC transformation that results may be used to update model-to-PSC transformation 295. The updated model-to-PSC transformation 295 may then be used with Equation 3 to determine the updated model-to-image transformation 255.

Figure 3A:
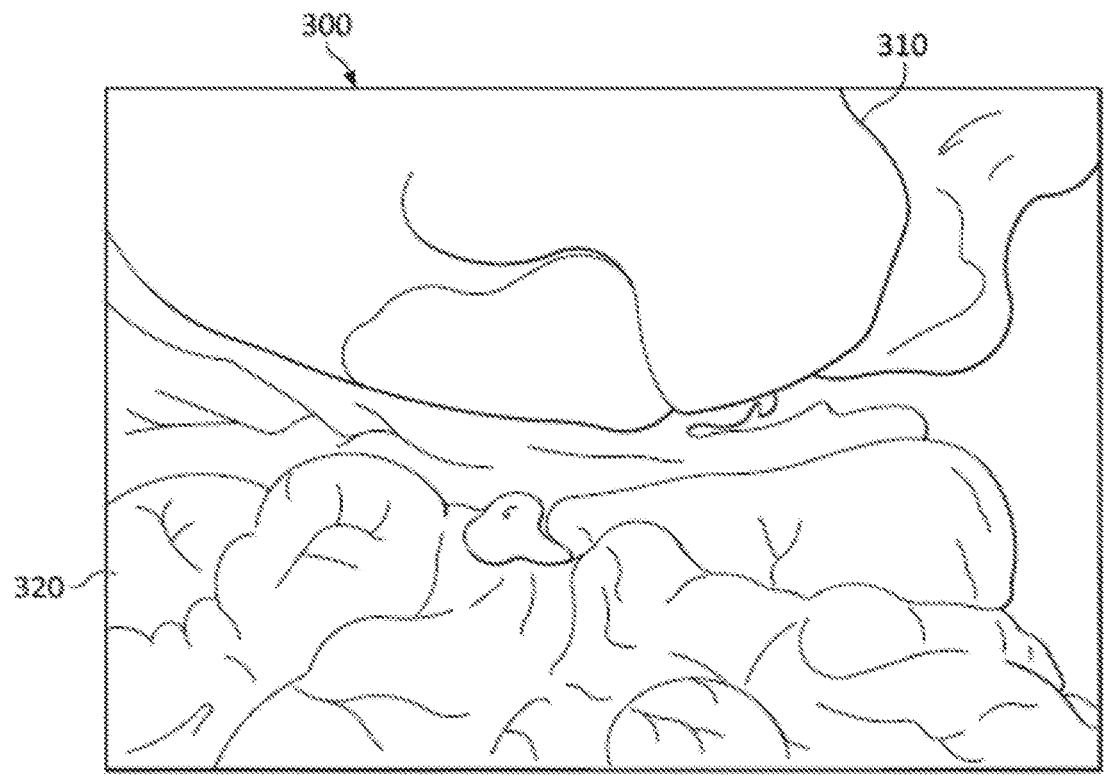
FIGS. 3A and 3B are simplified diagrams of displayable images generated according to some embodiments.
Figure 3B:
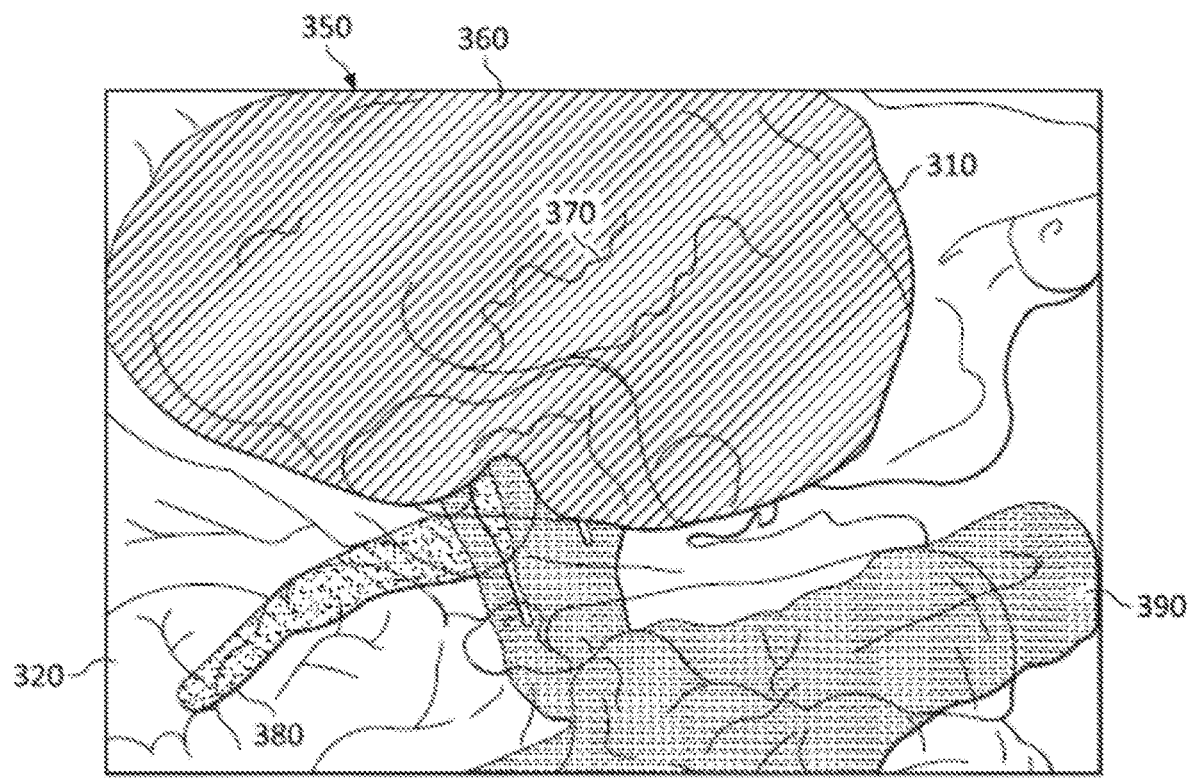

FIGS. 3A and 3B are simplified diagrams of displayable images generated according to some embodiments. FIG. 3A includes a simplified rendition of an endoscope image 300 consistent with a partial nephrectomy procedure on a porcine. Visible within endoscope image 300 are a kidney 310 and nearby intestines 320. FIG. 3B includes a simplified rendition of a composite image 350 showing an overlay of a model of the corresponding anatomy over endoscope image 300 after registration of the model has occurred. In some examples, the model may be generated from CT angiographic imaging of the anatomy. Still visible within composite image 350 are kidney 310 and intestines 320. Also included within composite image 350 are semi-transparent elements from the model including the parenchyma 360 of kidney 310 as well as non-visible elements including internal structures 370 of kidney 310, ureter 380, and vasculature 390. As shown, each of the different elements from the model (parenchyma 360, internal structures 370, ureter 380, and vasculature 390) is shown using different patterns to help the operator distinguish between different structures, in some examples, other visual differentiating techniques may also be used, such as false coloring. In some examples, semi-transparency of the model elements may be obtained using techniques such as alpha blending and/or the like. Overlay of the model elements on endoscope image 300 as shown in composite image 350 allows the operator to simultaneously visualize the interior and hidden structures of the anatomy from the model in correct relationship with visible anatomy from endoscope image 300. This allows, for example, the operator to avoid areas of the anatomy during a procedure, to identify hidden features (e.g., a lesion), and/or the like. And although only one endoscope image 300 and composite image 350 are shown in FIG. 3, when stereoscopic imaging is used, both left and right versions of these images would be generated of which endoscope image 300 and composite image 350 are representative examples.

As discussed above and further emphasized here, FIGS. 3A and 3B are merely examples which should not unduly limit the scope of the claims. One of ordinary skill in the art would recognize many variations, alternatives, and modifications. In some embodiments, other arrangements and configurations of endoscope image 300 and/or composite image 350 are possible. In some examples, composite image 350 may include the model rendered as a picture within picture and/or inset picture within the endoscope image. In some examples, composite image 350 may include the model rendered above, below, to the right of, and/or to the left of the endoscope image. In some examples, endoscope image 300 may be obtained using fluorescence imaging and/or multi-spectral imaging and may include images of one or more subsurface anatomical structures, such as lesions, tumors, vasculature, ducts, calyces, and/or the like.

Figure 4:
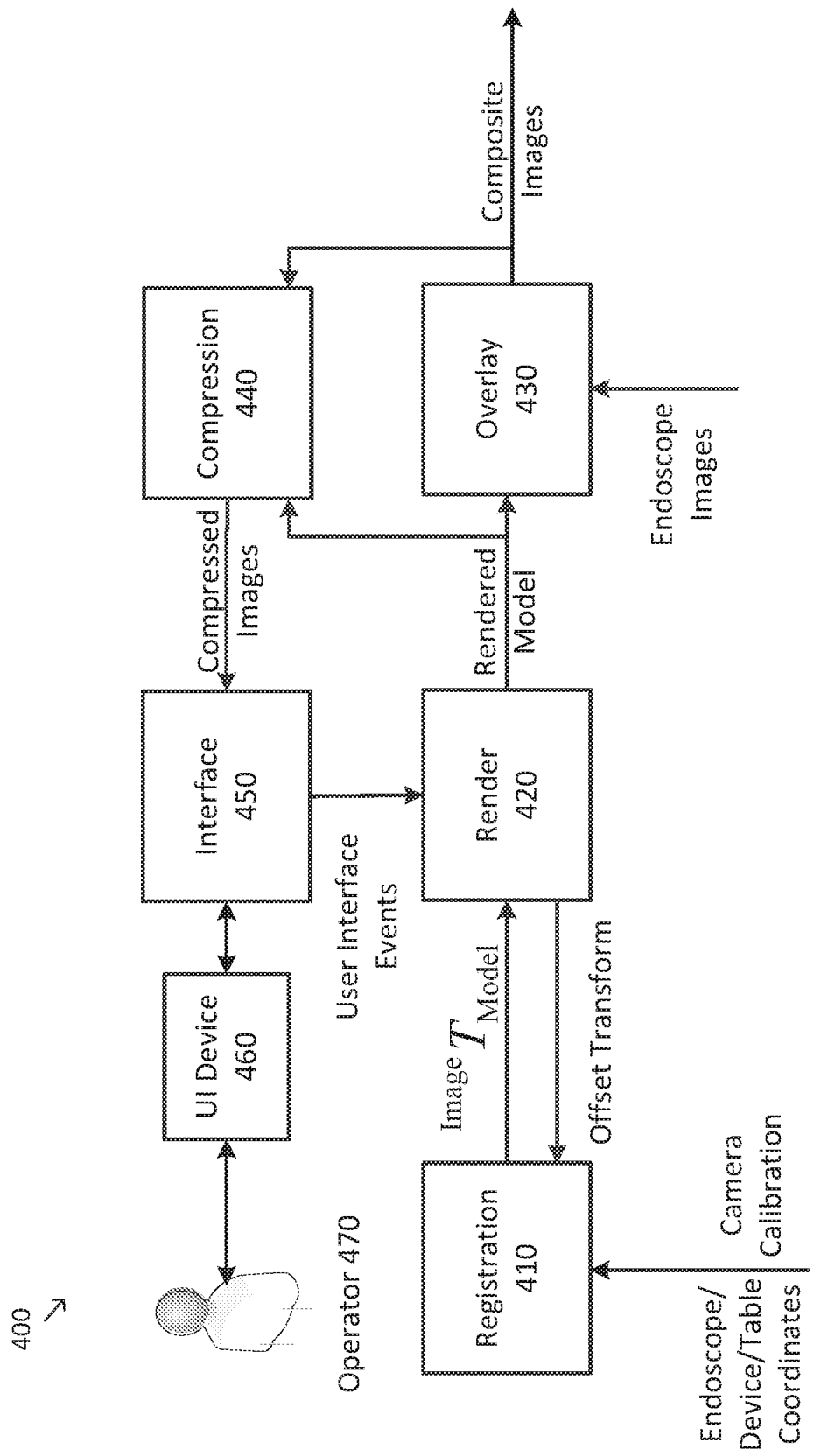
FIG. 4 is a simplified diagram of a data flow model for generating overlay images according to some embodiments.

FIG. 4 is a simplified diagram of a data flow model 400 for generating overlay images according to some embodiments. In some embodiments, data flow model 400 may be implemented using control unit 130, imaging application 160, and UI device 190 of FIG. 1. As shown in FIG. 4, data flow model 400 includes a registration module 410, a rendering module 420, an overlay module 430, an optional compression module 440, an interface module 450, and a UI device 460.

Registration module 410 receives kinematic data (e.g., endoscope, computer-assisted device, and table coordinates and sensor values) and/or calibration data for the endoscope. Registration module 410 uses these to compute various transformations, such as the transformations of Equations 1, 2, and 3. Registration module 410 then uses the transformations to determine the baseline model-to-PSC transformation and to generate updates to the model-to-image transformation that is used to overlay model elements on endoscope images. Registration module 410 also receives an offset transformation from rendering module 420 that are derived from inputs received from an operator 470 on UI device 460 as part of the registration process.

Rendering module 420 renders the model in the endoscope image coordinate system (e.g., endoscope image coordinate system 250) so that the overlay of the model onto the endoscope image continues to match the underlying anatomy as established by the registration process. Rendering module 420 further renders the model subject to the adjustments made by operator 470 during the registration process. Rendering module 420 receives these adjustments as user interface events received from UI device 460 via interface module 450.

Overlay module 430 receives the transformed and rendered model from rendering module 420 and overlays them onto endoscope images from the endoscope to form composite images. Overlay module 430 generates the composite images during both the registration process and the subsequent tracking. The model is overlaid onto the endoscope images so that it appears semi-transparent, as for example shown in composite image 350. In some examples, overlay module 430 uses alpha blending and/or the like to generate the composite images. The composite images are then sent to a display device, such as a stereoscopic viewer, for display to operator 470 and/or other personnel.

Optional compression module 440 compresses the composite image and/or the rendered model in order to reduce storage and/or bandwidth used by the composite images and/or the rendered model. In some examples, compression algorithms such as JPEG, and/or the like may be used during the compression.

Interface module 450 distributes the compressed images to at least UI device 460. Interface module 450 may include one or more networking and/or other APIs for sharing the compressed images via a network. Interface module 450 also receives user interface events from UI device 460 and forwards them to rendering module 420 to support the registration process. Although not shown, interface module 450 and/or a separate interface module may be used to distribute the composite images generated by overlay module 430 and that are sent to the display device.

UI device 460 is used, among other things, to display the composite images to operator 470 dining the registration process. As operator 470 manipulates the model via various interactions with UI device 460, UI device 460 forwards these via interface module 450 to rendering module 420. These interactions are used to adjust a position and/or orientation of the model during the registration process as is described in further detail below. UI device 460 may also be used to control the appearance and/or display modes of the composite images during both the registration process and/or tracking. In some examples, UI device 460 may be a touchscreen device, such as an iPad or tablet, a telestrator, and/or the like.

Figure 5:
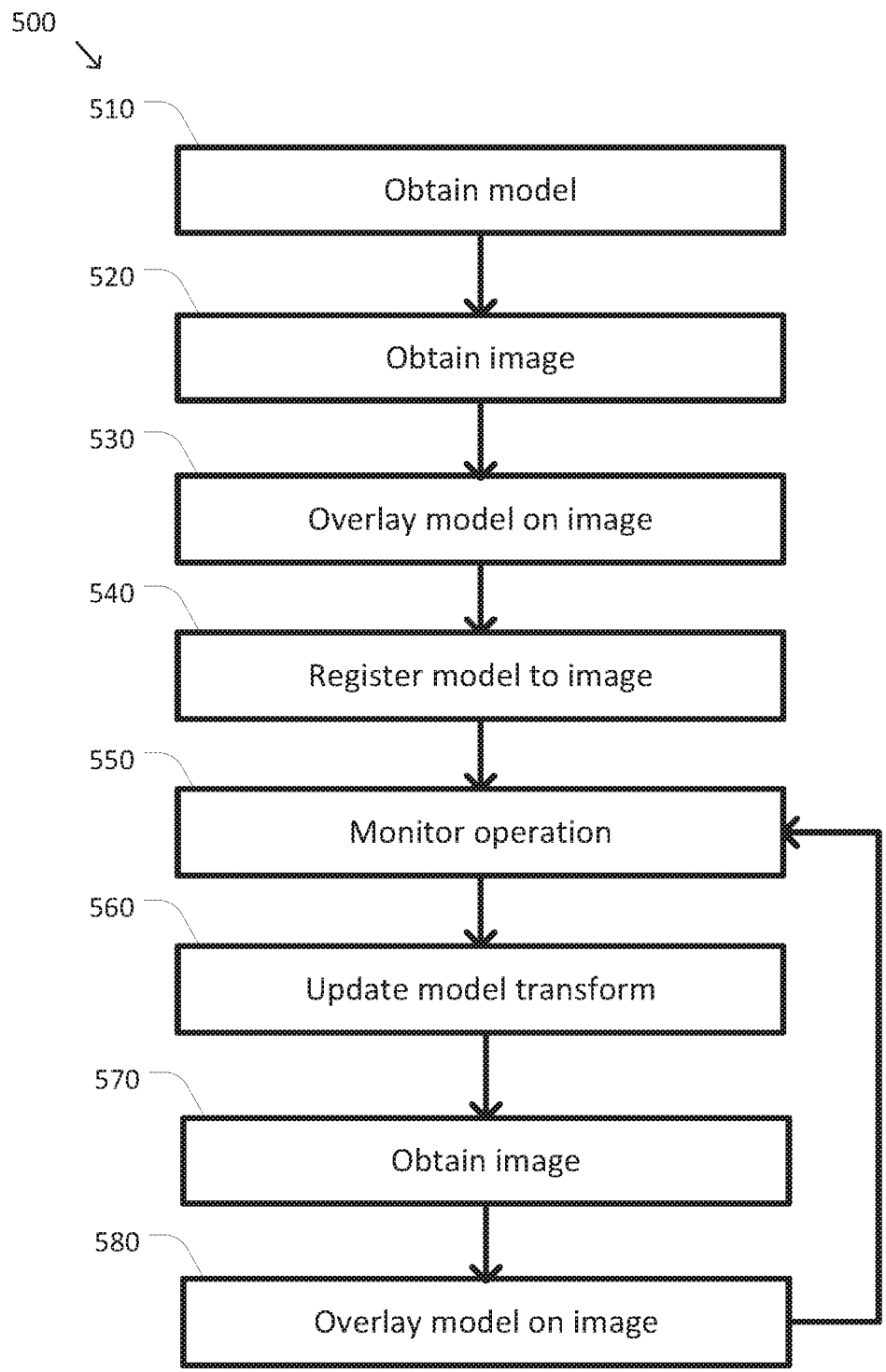
FIG. 5 is a simplified diagram of the method of overlaying images according to some embodiments.

FIG. 5 is a simplified diagram of the method 500 of overlaying images according to some embodiments. One or more of the processes 510-580 of method 500 may be implemented, at least in part, in the form of executable code stored on non-transient, tangible, machine readable media that when run by one or more processors (e.g., the processor 140 in control unit 130) may cause the one or more processors to perform one or more of the processes 510-580. In some embodiments, method 500 may be used to generate composite images, such as composite image 350, which overlay a semi-transparent model of anatomy onto images of the anatomy captured by an endoscope. In some embodiments, method 500 may be implemented using data flow model 400. In some embodiments, one or more of processes 510-580 may be performed in an order other than the implied order of FIG. 5 and/or may include additional processes as would be understood by one of ordinary skill in the art. In some examples, processes 520 and/or 530 may be performed concurrently with process 540. In some examples, process 570 may be performed concurrently with processes 550 and/or 560. And although method 500 is described below with respect to single images, it is understood that method 500 is adaptable to a stereoscopic vision system where corresponding left and right images may be generated according to the representative processes of method 500.

At a process 510, a model is obtained. In some examples, pre-operative or intra-operative image data of the anatomy of a patient is obtained using a suitable imaging technology such as, CT, MRI, fluoroscopy, thermography, ultrasound, OCT, thermal imaging, impedance imaging, laser imaging, nanotube X-ray imaging, and/or the like. The pre-operative or intra-operative image data may correspond to two-dimensional, three-dimensional, or four-dimensional (including e.g., time based or velocity based information) images. The image data is then used to determine the structure of the anatomy including surface features (such as a parenchyma and/or the like), interior features (such as ducts, calyces, and/or the like), target features (such as a tumor, lesion, and/or the like), and/or the like. In some examples, the model may be partitioned to identify different structures within the anatomy so that they may be selectively omitted from the model and/or rendered using a different pattern, false color, and/or the like. In some examples, the model may be normalized in size and/or maintained in a true-size coordinate system. In some examples, a centroid of the model may also be determined with the centroid being associated with the model as a whole or just to a subset of the structures within the model. In some examples, the determination of the centroid may depend on the anatomy involved, a procedure being performed, operator preference, and/or the like.

At a process 520, an image is obtained. In some examples, the image may be obtained using an imaging device, such as an endoscope, and may correspond to those portions of the anatomy that are visible to the imaging device. In some examples, the image may be consistent with endoscope image 300. In some examples, the imaging device should be positioned and/or oriented so as to capture images of the anatomy corresponding to the model obtained during process 510.

At a process 530, the model is overlaid on the image to create a composite image. In some examples, the model obtained during process 510 is initially overlaid onto the image obtained during process 520 according to a best-guess as to the relationship between the model and the image. In some examples, the centroid of the model determined during process 510 is overlaid on the image at a depth from the imaging device that roughly corresponds to a current focal length of the imaging device. In some examples, this depth may correspond to a location approximately 5 to 10 cm in front of the endoscope. In some examples, alpha blending and/or other suitable approach may be used to make the model semi-transparent so that when it is overlaid on the image, the content of the image is still visible despite the presence of the model within the composite image. In some examples, the model may by overlaid visually such that it includes patterning, false coloring, and/or the like in order to help the operator distinguish between the content of the model and the content of the image.

At a process 540, the model is registered to the image. In some examples, the operator uses one or more gestures and/or inputs on a UI device, such as UI device 190 and/or UI device 460, to manipulate the model so that the structures in the model match the corresponding portions of the anatomy visible in the image. In some examples, the inputs are used to control a depth (e.g., how far the model is from the anatomy as seen in the image), a position (e.g., a location of the model relative to a center of the image), and/or an orientation (e.g., a rotation of the model relative to the image). In some examples, various controls such as dials, sliders, and/or the like may be used to obtain the inputs.

According to some embodiments, various touchscreen and/or telestrator actions may be used to obtain the inputs. As an example, a two-finger pinch operation may be used to adjust the depth of the model with a pinching or closing gesture between the two fingers being used to move the model further from the endoscope and an opening gesture being used to move the model closer to the endoscope. Changing the depth of the model relative to the endoscope also gives the appearance of scaling the size of the model relative to the image. A two-finger drag operation may be used to translate the model left and right and/or up and down relative to the image. A two-finger rotate operation may be used to rotate within the plane of the image and thus change a roll orientation of the model relative to the image via a rotation about the direction of view. A one-finger drag operation may be used to control a yaw of the model (amount of horizontal drag) and/or a pitch (amount of vertical drag). Each of the rotations may occur either about the centroid of the model or about a coordinate system defined by the focal distance of the imaging device, the direction of view, and the view-up orientation of the image. A sensitivity of the manipulations to the model based on the amount of one- and/or two-finger movement may be set according to a procedure being performed, operator preference, and/or the like. When the operator is satisfied that the model is acceptably registered to the image, the operator may indicate this by activating an appropriate input (e.g., a button) on the UI device and/or some other input device associated with the system performing method 500.

During process 540, each of the manipulations of the model relative to the image is composited together to generate a model-to-image transformation, such as model-to-image transformation 255. Equation 1 may then be used to determine a baseline model-to-PSC transformation or equivalent transformation for use during later processes.

At a process 550, operation of a computer-assisted device used to perform the procedure is monitored. This includes determining whether there are any changes in the kinematic relationships of the computer-assisted device so that the effects of these changes in the model-to-image transformation may be accounted for.

At a process 560, the model-to-image transformation is updated. The monitored changes observed during process 550 are used to update the transformations that describe the kinematics of the computer-assisted device using the approach described previously with respect to FIG. 2. Equation 3 may then be used to update the model-to-image transformation so that the overlaid model may be automatically adjusted to track the movements so that the model remains registered to the image.

At a process 570, an image is obtained using a process similar to process 520, and at a process 580 the model is overlaid on the image using a process similar to process 530 with the overlay occurring according to the updated model-to-image transformation determined during process 560. Monitoring of the operation of the computer-assisted device continues by returning to process 550.

As discussed above and further emphasized here, FIG. 5 is merely an example which should not unduly limit the scope of the claims. One of ordinary skill in the art would recognize many variations, alternatives, and modifications. In some embodiments, method 500 may be adapted to account for observed motion in the surgical table and/or of the patient relative to the table, such as by using table registration and the determination of a table-to-PSC transformation as described with respect to FIG. 2. In some embodiments, method 500 may be altered to allow additional registration processes (e.g., by repeating processes 520-540). In some examples, an additional registration process may be initiated by the operator using a suitable input and/or by detection of the system that the model is no longer suitably matched to the image (e.g., by detecting excessive movement in the computer-assisted device and/or surgical table).

In some embodiments, one or more other imaging techniques may be used during method 500. In some examples, the registering of processes 520-450 may be performed with respect to an image obtained using a first imaging device installed on a first articulated arm of the computer-assisted device and the overlaying and composite image generation of processes 570 and 580 may be performed with an image obtained using a second imaging device installed on a second articulated arm of the computer-assisted device. In some examples, the image obtained during process 520 may be obtained using fluorescence imaging and/or multi-spectral imaging and may include images of one or more subsurface anatomical structures, such as lesions, tumors, vasculature, ducts, calyces, and/or the like. In some examples, the subsurface features highlighted by the fluorescence imaging and/or multi-spectral imaging may be used to support the registration of process 540.

Some examples of control units, such as control unit 130 may include non-transient, tangible, machine readable media that include executable code that when run by one or more processors (e.g., processor 140) may cause the one or more processors to perform the processes of method 500. Some common forms of machine readable media that may include the processes of method 500 are, for example, floppy disk, flexible disk, hard disk, magnetic tape, any other magnetic medium, CD-ROM, any other optical medium, RAM, PROM, EPROM, FLASH-EPROM, any other memory chip or cartridge, and/or any other medium from which a processor or computer is adapted to read.

Although illustrative embodiments have been shown and described, a wide range of modification, change and substitution is contemplated in the foregoing disclosure and in some instances, some features of the embodiments may be employed without a corresponding use of other features. One of ordinary skill in the art would recognize many variations, alternatives, and modifications. Thus, the scope of the invention should be limited only by the following claims, and it is appropriate that the claims be construed broadly and in a manner consistent with the scope of the embodiments disclosed herein.

What is claimed is:

1. A method of generating augmented reality images comprises:
    overlaying a model of patient anatomy to a first image of the patient anatomy that was captured using an imaging device such that a centroid of the model of patient anatomy is located along a direction of view of the imaging device at an initial depth based on a focal length of the imaging device;
    adjusting, based on one or more inputs received from a user, a depth of the model of patient anatomy relative to the first image of the patient anatomy along the direction of view;
    upon adjusting the model of patient anatomy, generating a baseline relationship between the model of patient anatomy and the first image of the patient anatomy;
    tracking movement of a computer-assisted device used to manipulate the imaging device;
    updating the baseline relationship based on the tracked movement of the computer-assisted device and a kinematic model of the computer-assisted device; and
    generating a composite image by overlaying, based on the updated baseline relationship, the model of patient anatomy on a second image of the patient anatomy.

2. The method of claim 1, further comprising rendering the model of patient anatomy so that the model of patient anatomy is semi-transparent.

3. The method of claim 1, wherein the model of patient anatomy is overlaid as a picture within the composite image.

4. The method of claim 1, wherein generating the baseline relationship comprises generating a model to image transformation based on the adjusted model of patient anatomy, the model to image transformation capturing the baseline relationship between the model of patient anatomy and the first image.

5. The method of claim 1, wherein:
the imaging device supports fluorescence imaging or multi-spectral imaging; and
the first image includes one or more subsurface anatomical structures highlighted by the fluorescence imaging or the multi-spectral imaging that are used to generate the baseline relationship.

6. A computer-assisted medical device comprising:
an articulated arm;
an imaging device mounted on the articulated arm; and
a processor coupled to the articulated arm and the imaging device, the processor being configured to:
overlay a model of patient anatomy on a first image of the patient anatomy that was captured using the imaging device such that a centroid of the model of patient anatomy is located along a direction of view of the imaging device at an initial depth based on a focal length of the imaging device;
adjust, based on one or more inputs received from a user, a depth of the model of patient anatomy relative to the first image along the direction of view;
upon adjusting the model of patient anatomy, generating a baseline relationship between the model of patient anatomy and the first image of the patient anatomy;
track movement of the articulated arm;
update the baseline relationship based on the tracked movement of the articulated arm and a kinematic model of the articulated arm; and
generate a composite image by overlaying, based on the updated baseline relationship, the model of patient anatomy on a second image of the patient anatomy.

7. The computer-assisted medical device of claim 6, processor is further configured to render the model of patient anatomy so that the model of patient anatomy is semi-transparent.

8. The computer-assisted medical device of claim 6, wherein the model of patient anatomy is overlaid as a picture within the composite image.

9. The computer-assisted medical device of claim 6, wherein generating the baseline relationship comprises generating a model to image transformation based on the adjusted model of patient anatomy, the model to image transformation capturing the baseline relationship between the model of patient anatomy and the first image.

10. The computer-assisted medical device of claim 9, wherein to register the model of patient anatomy to the first image, the processor is further configured to generate a baseline transformation between the model of patient anatomy and the computer-assisted medical device based on the model to image transformation.

11. The computer-assisted medical device of claim 10, wherein updating the baseline relationship is further based on the baseline transformation between the model of patient anatomy and the computer-assisted medical device.

12. The computer-assisted medical device of claim 9, wherein the processor is further configured to:
upon generating the composite image, receive one or more second inputs from the user; and
adjust, based on the one or more second inputs, a second relative position, a second relative orientation, or both, between the model of patient anatomy and the second image.

13. The computer-assisted medical device of claim 9, wherein the one or more inputs are based on one or two finger gestures by the user on a user interface device.

14. The computer-assisted medical device of claim 6, wherein the model of patient anatomy comprises anatomical features not visible in the first image.

15. The computer-assisted medical device of claim 6, wherein:
the imaging device supports fluorescence imaging or multi-spectral imaging; and
the first image includes one or more subsurface anatomical structures highlighted by the fluorescence imaging or the multi-spectral imaging that are used to generate the baseline relationship.

16. A non-transitory computer-readable medium having stored thereon a plurality of machine-readable instructions that, when executed by one or more processors associated with a computer-assisted device, are adapted to cause the one or more processors to perform a method comprising:
overlaying a model of patient anatomy on a first image of the patient anatomy that was captured using an imaging device such that a centroid of the model of patient anatomy is located along a direction of view of the imaging device at an initial depth based on a focal length of the imaging device;
adjusting, based on one or more inputs received from a user, a depth of the model of patient anatomy relative to the first image of the patient anatomy;
upon adjusting the model of patient anatomy, generating a baseline relationship between the model of patient anatomy and the first image of the patient anatomy;
tracking movement of the computer-assisted device used to manipulate the imaging device;
updating the baseline relationship based on the tracked movement of the computer-assisted device and a kinematic model of the computer-assisted device; and
generating a composite image by overlaying, based on the updated baseline relationship, the model of patient anatomy on a second image of the patient anatomy.

17. The non-transitory computer-readable medium of claim 16, wherein the method further comprises rendering the model of patient anatomy so that the model of patient anatomy is semi-transparent.

18. The non-transitory computer-readable medium of claim 16, wherein the model of patient anatomy is overlaid as a picture within the composite image.

19. The non-transitory computer-readable medium of claim 16, wherein generating the baseline relationship comprises generating a model to image transformation based on the adjusted model of patient anatomy, the model to image transformation capturing the baseline relationship between the model of patient anatomy and the first image.

20. The non-transitory computer-readable medium of claim 16, wherein:
the imaging device supports fluorescence imaging or multi-spectral imaging; and
the first image includes one or more subsurface anatomical structures highlighted by the fluorescence imaging or the multi-spectral imaging that are used to generate the baseline relationship.

21. The method of claim 1, further comprising adjusting, based on the one or more inputs received from the user, an orientation of the model of patient anatomy about the centroid of the model of the patient anatomy.

22. The method of claim 1, further comprising:
adjusting, based on the one or more inputs received from the user, the model of patient anatomy normal to the direction of view of the imaging device; and
adjusting, based on the one or more inputs received from the user, an orientation of the model of patient anatomy about the direction of view of the imaging device.

* * * * *